United States Patent [19]

Heilman et al.

[11] 4,303,075
[45] Dec. 1, 1981

[54] METHOD AND APPARATUS FOR MAXIMIZING STROKE VOLUME THROUGH ATRIOVENTRICULAR PACING USING IMPLANTED CARDIOVERTER/PACER

[75] Inventors: Marlin S. Heilman, Gibsonia; Alois A. Langer, Pittsburgh, both of Pa.

[73] Assignee: Mieczyslaw Mirowski, Owings Mills, Md.

[21] Appl. No.: 120,099

[22] Filed: Feb. 11, 1980

[51] Int. Cl.³ .............................................. A61N 1/36
[52] U.S. Cl. ........................... 128/419 PG; 128/419 D
[58] Field of Search ..................... 128/419 D, 419 PG

[56] References Cited

U.S. PATENT DOCUMENTS

| 3,716,059 | 2/1973 | Welborn et al. | 128/419 PG |
| 4,030,509 | 6/1977 | Heilman et al. | 128/419 D |
| 4,108,148 | 8/1978 | Cannon | 128/419 PG |
| 4,166,470 | 9/1979 | Neumann | 128/419 PG |
| 4,202,340 | 5/1980 | Langer et al. | 128/419 D |

FOREIGN PATENT DOCUMENTS 683722 9/1979 U.S.S.R. ...................... 128/419 PG

*Primary Examiner*—William E. Kamm
*Attorney, Agent, or Firm*—Fleit & Jacobson

[57] ABSTRACT

A method and apparatus for maximizing stroke volume through atrioventricular pacing using an implanted cardioverter/pacer accomplishes AV pacing with an AV delay tailored to the particular patient, thereby maximizing accuracy and efficiency. The invention involves the measurement of successive impedance changes, or swings, from one heart cycle to the next, across a pair of electrodes connected in proximity to the heart, the processing of the successive impedance changes to detect variations and directions of variations thereof, the issuance of atrial and ventricular pacing pulses, separated by a time interval therebetween, to the atria and to the ventricles, respectively, and the selective increasing or decreasing of the time interval between the atrial and ventricular pacing pulses in dependence on the directions of variation of the successive impedance changes to maximize impedance swings.

13 Claims, 6 Drawing Figures

METHOD AND APPARATUS FOR MAXIMIZING STROKE VOLUME THROUGH ATRIOVENTRICULAR PACING USING IMPLANTED CARDIOVERTER/PACER

BACKGROUND OF THE INVENTION

1. Field of the Invention

The present invention relates to a method and apparatus for maximizing stroke volume through atrioventricular pacing using an implanted cardioverter/pacer.

2. Description of the Prior Art

The ability to control heart rate by means of electrical stimulation has given the cardiologist an important tool for the management of patients suffering from abnormal heart functioning. Medical technology has developed to the point that battery-operated pacers, both temporary and implantable, are available with characteristics suitable for various clinical situations. The operation of such heart pacers (also known as pacemakers) presupposes basic understanding of the functioning of the heart.

The heart is divided into a left atrium, right atrium, left ventricle and right ventricle, and contains a sinoatrial (SA) node, which is a region of specialized tissue in the wall of the right atrium. This is the natural pacemaker of the heart, in that it emits a series of electrical pulses, each of which triggers a cycle of cardiac activity. As the pulse from the SA node spreads across the atrial walls, it initiates atrial contraction to pump blood into the ventricles. The pulse is then detected by another area of specialized tissue, known as the atrioventricular (AV) node, and is then conducted through special pathways of conductive tissue to the ventricles. While the pulse passes through the conductive tissues to the walls of the ventricles, atrial contraction moves blood into the ventricles. By the time ventricular contraction begins (as a result of arrival of the pulse at the ventricles), the ventricles are expanded and ready to pump blood into the lungs and the circulatory system of the body. After each contraction, the heart relaxes, the atria refill with blood, and another pulse is generated in the SA node so as to start the next cycle of cardiac activity.

Normal rhythm (known as "sinus rhythm") originates in the SA node of the heart. However, disorders of rhythm (known as "arrhythmias") may occur. For example, if the conductive pathways to or in the ventricles are for any reason disrupted, atrial-generated pulses may no longer trigger ventricular activity, and ventricular contraction may no longer be synchronized with atril activity. There are numerous arrhythmias wherein the normally sequential contractions of the atria and the ventricles are absent. Such arrhythmias have led to the development of the electronic pacemaker, which takes over the task of stimulating the ventricles to contract at a normal rate (for example, 70 beats per minute). In the modern demand electronic pacemakers, operation is typically synchronized with the heart's electrical activity through electrocardiograph (ECG) monitoring.

The normal ECG consists of a series of voltage changes resulting from the contraction of the atria and the contraction and recovery of the ventricles in the heart. A normal electrocardiogram derived from ECG monitoring includes a series of spaced waveform regions known as the QRS complex, consisting of: a small upward deflection (the P wave), due to atrial contraction; a brief downward swing (the Q wave), followed by a large upward swing (the R wave), and then a further downward swing (the S wave), resulting from ventricular contraction; and a small upward deflection (the T wave), indicating recovery of the ventricles. Thus, disturbances of the conducting mechanism or pathways between the atria and the ventricles (known as "heart blocks") can be detected by ECG monitoring. When the rate of conduction from the AV node down through the conductive pathways is prolonged, the P-R interval is longer than normal, and this is called a first degree atrioventricular (AV) block. Another type of arrhythmia (incomplete heart block or second degree block) occurs when the ventricles do not respond to every atrial beat. Such a situation can be caused by too fast an atrial rate, or by a diseased AV pathway, and can be detected by ECG monitoring. Finally, a complete heart block (or complete AV dissociation) occurs when the main conducting pathway between the atria and ventricles is interrupted. In such situation, the atria continue to beat normally, but the ventricles beat at their own, often very slow, escape rate, and such a situation can also be detected by ECG monitoring. Occurrence of any of the latter conditions indicates need for artificial stimulation of the heart.

The concept of atrioventricular (AV) pacing was developed to combat the latter-noted heart disturbances. As an example, one type of AV pacer typically operates as follows. The AV pacer monitors the electrical activity of the heart and awaits a ventricular contraction (as indicated by an R wave in the ECG). If no ventricular contraction occurs after a first period of time (known as the "atrial escape interval"), the pacer issues a stimulation pulse, which is applied to the atrium of the heart. Then, the pacer again awaits a ventricular contraction. If, by the end of a second period of time (known as the "ventricular escape interval") there is no ventricular contraction, a ventricular stimulation pulse is generated, and is applied to the ventricle of the heart. The difference in time between the atrial escape interval and the ventricular escape interval equals the delay between issuance of the atrial pulse and the ventricular pulse, and is known as the "AV delay." The normal heart typically issues atrial and ventricular pulses with a natural AV delay of 150-250 milliseconds.

In the modern AV pacer, the electronics are preprogrammed so that a fixed AV delay is set into the device, typically in the range of the aforementioned 150-250 milliseconds. Because hearts vary from individual to individual, a given AV delay may be optimum for one person, while the same delay may be only adequate for another. This less than optimum timing of the ventricular stimulation pulse could result in less than optimum pumping action by the paced heart. There is a need, therefore, for an electronic pacer which maximizes the amount of blood pumped by the heart (or "stroke volume") for each ventricular stimulation pulse.

SUMMARY OF THE INVENTION

The present invention relates to a method and apparatus for maximizing stroke volume through atrioventricular (AV) pacing using an implanted cardioverter/pacer. More particularly, the invention relates to a method and apparatus for AV pacing, wherein the spacing between the atrial and the ventricular pulses is adjustable and is accomplished independently of QRS detection and heart rate calculations, thus maximizing accuracy and efficiency.

In general terms, the method and apparatus of the present invention call for increasing or decreasing the interval between the atrial and ventricular stimulation pulses (AV delay) in accordance with detection of increasing or decreasing stroke volumes, as measured or detected from one heart cycle to the next. According to the invention, stroke volume is monitored by measuring the impedance between a pair of electrodes connected to, or in proximity with, the heart, and by processing the variation of such impedance so as to develop a parameter proportional to stroke volume. Moreover, a feedback loop is provided, and is functional to maximize stroke volume.

Thus, the present invention accomplishes AV pacing in such a manner that the AV delay is tailored to a particular patient. As a result, the present invention is able to achieve superior accuracy with respect to the techniques employed in the prior art.

Furthermore, since the present invention employs impedance processing, and since impedance processing is also a useful back-up technique for detecting ventricular fabrillation, the present invention provides the capability of integrally incorporating AV pacing and fabrillation detection (and defibrillation) into a single device. With respect to impedance sensing, it is known that the impedance across a normal heart rises and falls in a regular (pulsatile) fashion, while during ventricular fibrillation, such pulsatile impedance changes are minimal or absent. Thus, the impedance processing can serve both the purpose of AV pacing and the purpose of fibrillation detection.

Accordingly, it is an object of the present invention to provide a method and apparatus for maximizing stroke volume through atrioventricular pacing using an implanted cardioverter/pacer.

It is an additional object of the present invention to provide a method and apparatus which perform AV pacing in such a manner that the AV delay is tailored to a particular patient, thus achieving maximum accuracy in the process.

It is an additional object of the present invention to provide a method and apparatus which utilize impedance processing for the purpose of performing AV pacing.

It is an additional object of the present invention to provide a method and apparatus for AV pacing, while at the same time providing fibrillation detection and defibrillation when necessary.

The above and other objects that will hereinafter appear, and the nature of the invention, will more clearly be understood by reference to the following description, the appended claims, and the accompanying drawings.

DETAILED DESCRIPTION

The invention of the application will now more fully be described with reference to FIGS. 1 and 2 of the drawings.

Figure 1:
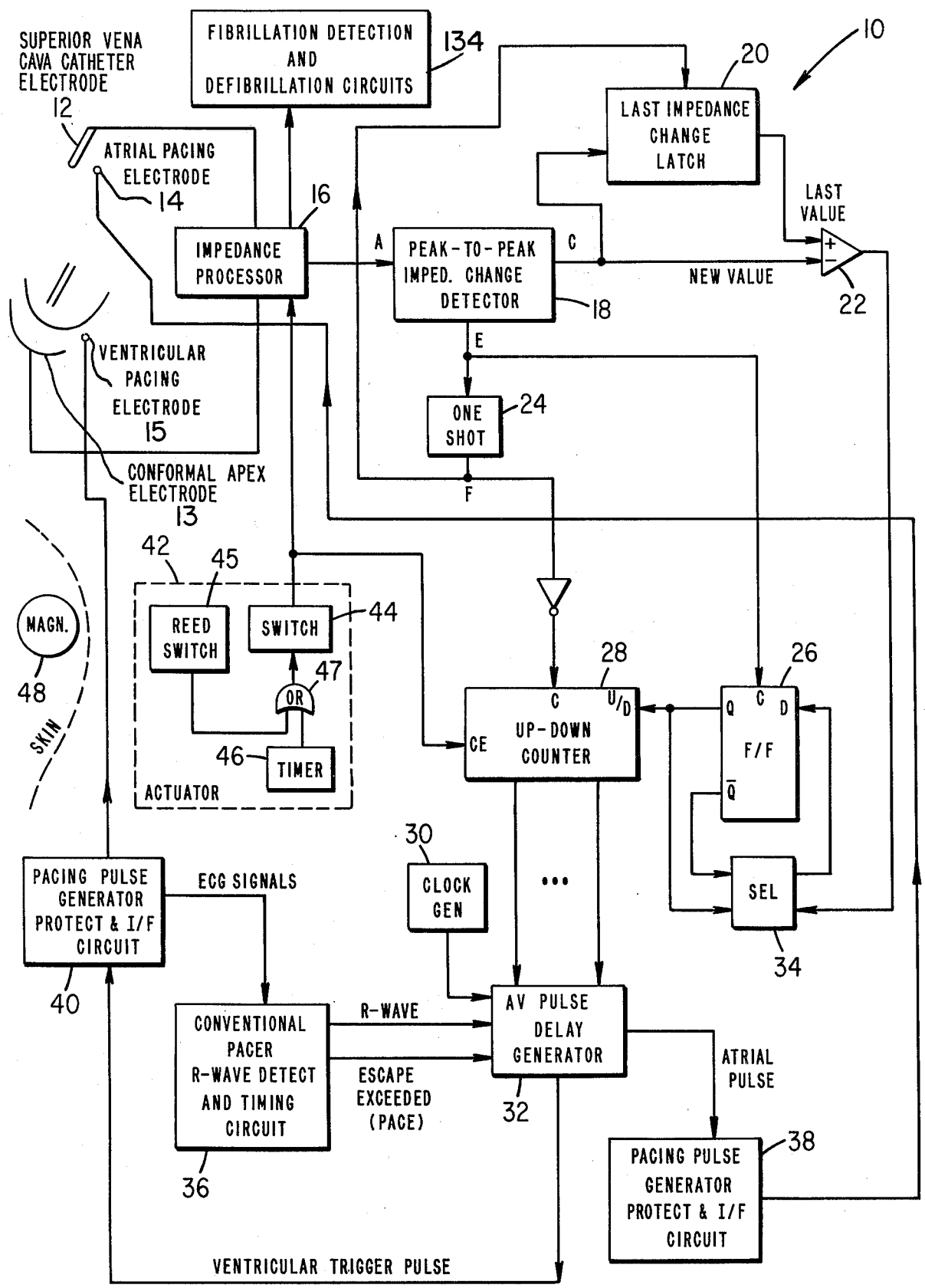
FIG. 1 is a diagrammatic representation of the inventive apparatus for atrioventricular pacing.

Referring to FIG. 1, the atrioventricular (AV) pacer is shown at 10 and comprises a pair of electrodes 12 and 13 (and corresponding leads), atrial and ventricular pacing electrodes 14 and 15, respectively (and corresponding leads), an impedance processor 16, a peak-to-peak impedance change detector 18, a last impedance change latch 20, a comparator 22, a one-shot circuit 24, a flip-flop 26, an up-down counter 28, a clock generator 30, an AV pulse delay generator 32, a selector 34, a conventional pacer 36, protective interface circuits 38 and 40, and an actuator 42.

Electrodes 12 and 13 are shown, respectively, as a superior vena cava catheter electrode and a conformal apex electrode, connected to or in proximity to the heart. For example, electrodes 12 and 13 could be of the type disclosed in the commonly assigned Heilman et al U.S. Pat. No. 4,030,509, and applications of Langer et al, Ser. Nos. 878,005 (now U.S. Pat. No. 4,202,340) and 878,006 (now U.S. Pat. No. 4,184,493), filed on Feb. 15, 1978.

The impedance of the heart, as measured by electrodes 12 and 13, varies between high and low values in accordance with the relative absence or presence of blood therein. The impedance is detected and processed by impedance processor 16, which emits an analog signal representing the fluctuating impedance of the heart. The impedance of the heart fluctuates between a minimum value (corresponding to presence of blood in the heart just prior to a contraction cycle) and a maximum value (corresponding to the absence of blood in the heart just subsequent to a contraction cycle). The change or swing in values between maximum and minimum impedance is porportional to the "stroke volume" of the heart.

The analog signal from impedance processor 16 is provided to peak-to-peak impedance change detector 18, which produces a voltage proportional to the peak-to-peak swing in the fluctuating impedance value measured by electrodes 12 and 13, and provided by impedance processor 16. It is the peak-to-peak swing voltage which approximates the stroke volume of the heart. Peak-to-peak detector 18 also generates a pulse output which indicates when the stroke volume data is valid, i.e., at its maximum value. The voltage output of peak-to-peak detector 18 is provided as an input (NEW VALUE) both to last impedance change latch 20 and to the negative input of comparator 22. Last impedance change latch 20 stores each NEW VALUE output of detector 18 for one cycle, and provides same to the positive input of comparator 22 as output LAST VALUE. Comparator 22 then performs a comparison operation between the last impedance swing value of latch 20 and the new impedance swing value of detector 18. As a result of the comparison operation, comparator 22 generates either a "low" or "high" output, and provides such output to selector 34.

Selector 34 is associated with flip-flop 26, and has its inputs connected, respectively, to the Q and $\overline{Q}$ outputs of the flip-flop 26. Dependent on the input from comparator 22, the selector 34 (as will be seen below) feeds either the Q output or the $\overline{Q}$ output to the D input of flip-flop 26. Thus, flip-flop 26 is caused either to maintain its present state or to change to its other state.

By virtue of its Q output being either "low" or "high", flip-flop 26 controls the up-down counter 28 so as to cause the latter to selectively count in the same direction as during the preceeding heart beat (when the new impedance swing value exceeds the previous impedance swing value) or to count in the opposite direction (when the new impedance swing value does not exceed the previous impedance swing value). Up-down counter 28 counts in accordance with a clock input from one-shot 24 (used as a delay element), as enabled by actuator 42.

The up-down counter 28 maintains a count value representing desired AV pulse delay, as provided to AV pulse delay generator 32. AV pulse delay generator 32, under the influence of conventional pacer 36, generates an atrial pulse if the atrial escape interval has been exceeded, which atrial pulse is provided, via protection and interface circuitry 38, to the atrial pacing electrode 14. Then, based on the AV delay provided to the generator 32 by the counter 28, the generator 32, after counting out the number of clock cycles represented by the digital input from counter 28, generates a ventricular trigger pulse, assuming no ventricular response to atrial contraction occurs. The trigger pulse is converted to a pacing pulse and is provided, via protection and interface circuitry 40, to the ventricular pacing electrode 15. As seen in FIG. 1, generator 32 is connected to receive an "escape exceeded" (pace) output from the conventional circuitry in pacer 36, which is connected at its input to the output of protection and interface circuitry 40 to provide a source of ECG signals from the ventricular electrode. If, after an atrial pacing pulse, a ventricular response is seen, the R-wave line inhibits the production of a ventricular pulse.

Thus, the AV pulse delay set in AV pulse delay generator 32 is varied (increased or decreased) by means of the up-down counting operation performed by counter 28 under the influence of flip-flop 26, and the AV pulse delay generator 32 utilizes the set AV pulse delay to generate atrial and ventricular pulses with such delay.

In a preferred embodiment, the pacer 10 includes an actuator 42 for issuing a signal to actuate both the impedance processor 16 and the up-down counter 28. The actuator 42 comprises a switch 44 for issuing the actuation command signal in response to a "high" output from OR gate 47, and a reed switch 45 and timer 46 connected to respective inputs of the OR gate 47. In operation, one of two actuation modes may be employed: (1) the "timer" mode by which switch 44 is caused, at predetermined time intervals, to issue its actuation command signal, and (2) the "command" mode, by which a magnet 48 (located externally of the body) may be brought into proximity to reed switch 45 so as to actuate same, causing generation of an actuation command signal by switch 44 (via OR gate 47). Thus, impedance processing by processor 16 and counting by counter 28 may be initiated at timed intervals (mode (1)), or on command (mode (2)).

Figure 2:
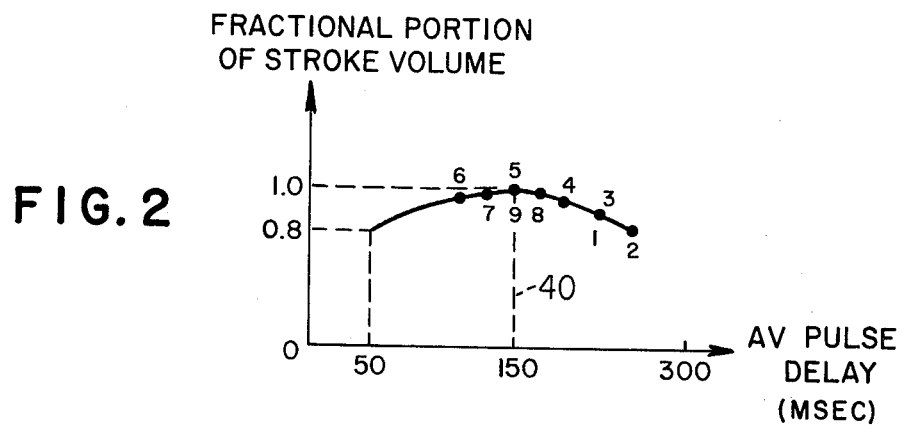
FIG. 2 is a graphical illustration of stroke volume versus AV delay.

Referring to FIG. 2, which is a graphical plot of fractional portion of stroke volume versus AV pulse delay (in milliseconds), it can be seen that there is an optimum value of AV pulse delay (approximately 150 milliseconds) at which peak performance, in terms of the fractional portion of stroke volume achieved by the heart, is obtained. Thus, impedance processor 16 and peak-to-peak detector 18 function to determine successive impedance swing values, that is, successive values of the swing in impedance from maximum to minimum.

Then, comparator 22 compares the previous impedance swing value with the current impedance swing value to determine the trend (increasing or decreasing impedance swing values). An increase or decrease in stroke volume can, thus, be detected.

In general, when an increase in stroke volume is detected, the output of detector 18 exceeds the output of latch 20, comparator 22 issues a negative or "low" output, flip-flop 26 maintains its current state, and up-down counter 28 is caused to continue to count in the same direction, so that stroke volume continues to increase as the optimum AV pulse delay is sought. Conversely, when decreasing stroke volume is detected, the output of latch 20 is greater than the output of detector 18, comparator 22 issues a positive or "high" output, flip-flop 26 is caused to change state, and up-down counter 28 is caused to reverse its direction of count, thus seeking an increase in stroke volume and the optimum value of AV pulse delay.

More specifically, in accordance with the present invention, the AV pacer 10 will, beginning at any initial point on the curve shown in FIG. 2, approach the point (9) of optimum AV pulse delay for maximizing stroke volume. Thus, considering that, at initial conditions, last impedance change latch 20 contains a value of zero, comparator 22 detects that the new value is greater than the last value, and issues a negative or "low" output to selector 34.

Figure 6:
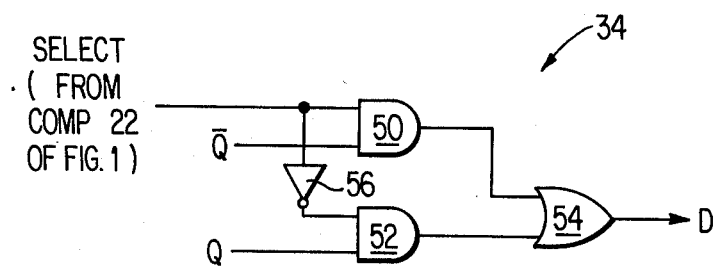
FIG. 6 is a logic diagram of the selector 34 of FIG. 1.

FIG. 6 shows a preferred embodiment of the selector 34, the latter comprising AND gates 50 and 52, OR gate 54, and inverter 56 connected to the input of AND gate 52 so as to invert the SELECT input, that is, the output of comparator 22 of FIG. 1, prior to provision to the input of AND gate 52. As seen in FIG. 6, AND gate 50 receives the $\overline{Q}$ output of flip-flop 26, while AND gate 52 receives the Q output from flip-flop 26.

Returning to consideration of the initial conditions, when comparator 22 detects that the new value is greater than the last value (arbitrarily set to zero), comparator 22 issues a negative (logic zero) output which causes AND gate 52 (FIG. 6) to provide the Q output of flip-flop 26 to the D input thereof. Thus, flip-flop 26 is kept in its present state and the direction of count remains the same.

Let us consider that the present (that is, initial) state of flip-flop 26 is the Q=1 state, calling for upcounting by counter 28, thus causing an increase in AV pulse delay. Under those conditions, the next point (in FIG. 2) will be point 2, and the new value of stroke volume will be less than the last value of stroke volume. Accordingly, comparator 22 will provide a positive (logic 1) output to the selector 34, thus enabling AND gate 50 to pass $\overline{Q}$ to the D input of flip-flop 26. This will cause flip-flop 26 to change state from Q=1 to Q=0 on the rising edges of output waveform E (FIG. 3), and the counter 28 will be placed in the down-counting mode.

Further referring to FIG. 2, in this manner, the AV pulse delay will be caused to successively decrease through positions 3, 4 and 5. Position 5 represents the optimum stroke volume and, thus, the optimum AV pulse delay (in this case, 150 milliseconds). It will be seen, from FIG. 2, that a further decrease in AV pulse delay to position 6 will cause the new value of peak-to-peak impedance change (corresponding to stroke volume) to be less than the last impedance change value, and comparator 22 will produce a positive (logic 1) output to the selector 34, causing the $\overline{Q}$ output of flip-flop 26 to be passed to the D input thereof, causing flip-flop 26 to change state from Q=0 to Q=1. Thus, up-down counter 28 will be placed in the up-counting mode, and the bracketing, or hunting, operation of the AV pacer 10 will continue through positions 7, 8 and 9 in FIG. 2.

Figure 4:
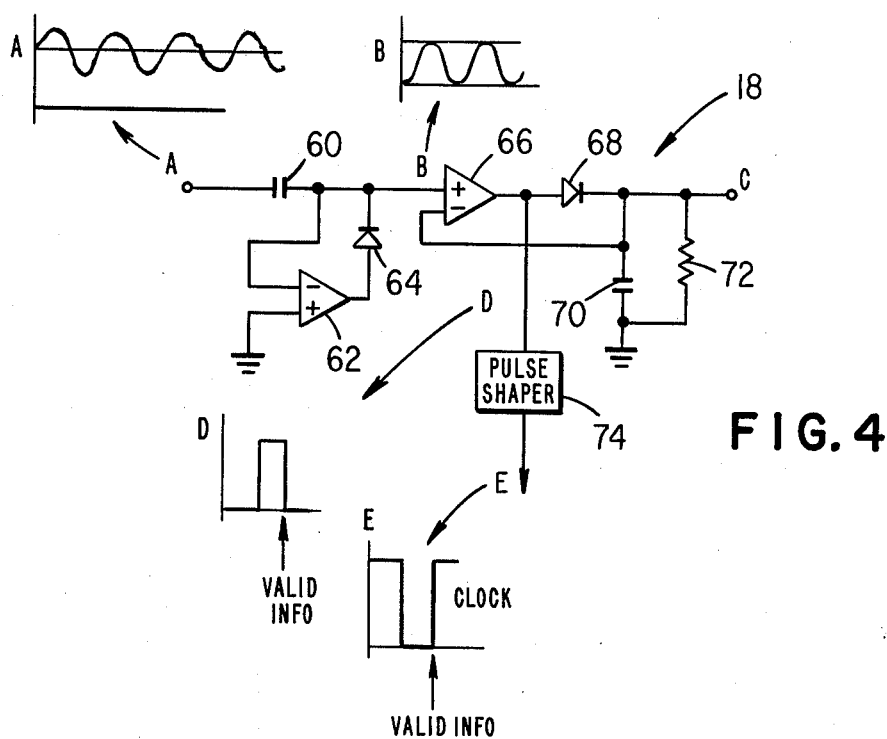
FIG. 4 is a schematic of the peak-to-peak impedance change detector 18 of FIG. 1.

FIG. 4 is a detailed diagram of the peak-to-peak impedance change detector 18 of FIG. 1. As seen therein, detector 18 comprises capacitors 60 and 70, differential amplifiers 62 and 66, diodes 64 and 68, resistor 72, and pulse shaper 74. In operation, capacitor 60, amplifier 62 and diode 64 clamp the input waveform A to a zero reference, producing output waveform B.

Figure 3:
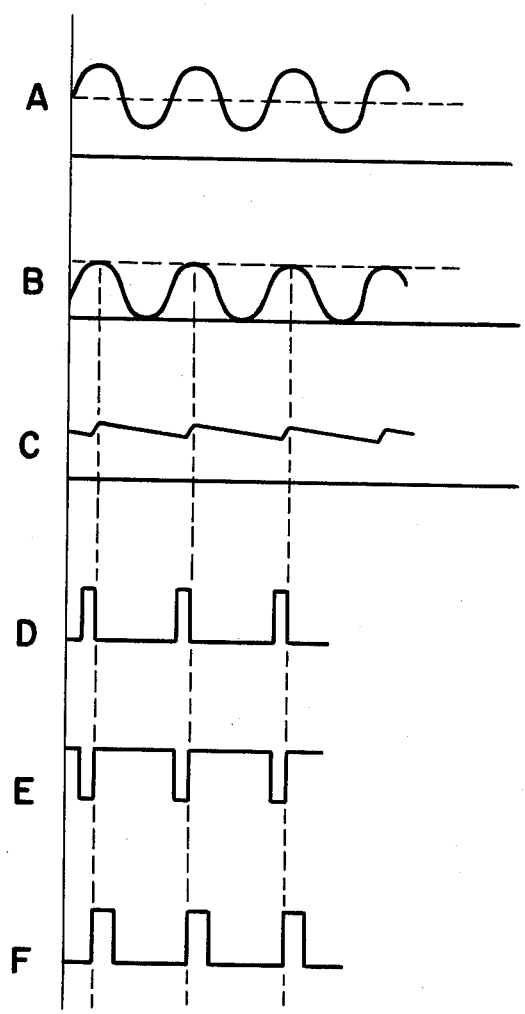
FIG. 3 is a timing diagram of the operation of the inventive apparatus of FIG. 1.

Further referring to FIGS. 3 and 4, signal B is provided to the positive input of amplifier 66, the negative input of which is feedback-connected to the output of diode 68, the latter having its input connected to the output of amplifier 66. Thus, amplifier 66 and diode 68 produce output waveform C, which is merely a peak-detected version of a maximum stroke volume, that is, the maximum change in values between maximum and minimum peaks of the waveforms A and B.

Furthermore, the output D of amplifier 66 (a square pulse which, via its trailing edge, indicates the presence of valid stroke volume information, i.e., maximum impedance change) is provided to pulse shaper 74, wherein it is inverted and formed into a "cleaner" pulse, producing output E. As mentioned earlier, output E is provided as a clock input to flip-flop 26, and also as an input to one-shot 24. Moreover, negative-going pulse E indicates valid information via its positive-going edge.

Figure 5:
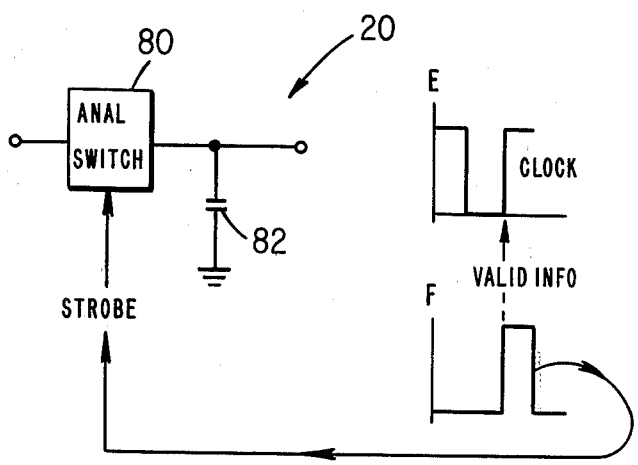
FIG. 5 is a schematic of the last impedance change latch 20 of FIG. 1.

FIG. 5 is a detailed schematic of a preferred embodiment of the last impedance change latch 20 of FIG. 1. As seen in FIG. 5, the last impedance change latch 20 comprises a conventional analog switch 80, the output of which is connected via a capacitor 82 to ground.

Referring to FIGS. 3 and 5, in operation, analog switch 80 receives the output C (NEW VALUE) from peak-to-peak impedance change detector 18 (FIG. 1), and passes that signal to output capacitor 82 in response to a strobe input. Specifically, the strobe input which actuates analog switch 80 is the output pulse F from one-shot 24; that is to say, the negative-going edge of pulse F strobes analog switch 80 so as to pass the output NEW VALUE from detector 18 to the output capacitor 82. In this manner, the NEW VALUE from detector 18, after a time delay (corresponding to the duration of the pulse F), becomes the input LAST VALUE to the positive input of comparator 22.

From the foregoing, it can be seen that superior results in terms of AV pacing are achieved by means of the present invention. Employment of the impedance processor 16 (FIG. 1) of the present invention results in two major advantages. Firstly, superior accuracy in setting AV pulse delay is achieved in a manner which is adjustable to suit the precise physiological needs of the patient. Secondly, by the employment of impedance processor 16 in AV pacer 10, the present invention is able to obtain the additional advantage of providing, by means of the same circuitry coupled with fibrillation detection and defibrillation circuits 134, both AV pacing and ventricular fibrillation detection (impedance processor 16 is of the type which is also useful in ventricular fibrillation detection and ventricular defibrillation, as disclosed in the aforementioned Application Ser. No. 878,005). Thus, a significant hardware saving to perform these two functions has been achieved.

While preferred forms and arrangements have been shown in illustrating the invention, it is to clearly be understood that various changes in detail and arrangement may be made without departing from the spirit and scope of this disclosure.

We claim:

1. A method of maximizing stroke volume of a heart through atrioventricular pacing using a pair of electrodes connected in proximity to the heart and an implanted cardioverter/pacer emitting pacing pulses, comprising the steps of:
   measuring successive impedance changes across said electrodes from one heart cycle to the next;
   processing said successive impedance changes to detect directions of variation thereof;
   issuing atrial and ventricular pacing pulses, separated by a time interval therebetween, to the atria and to the ventricles, respectively, of the heart; and
   selectively increasing or decreasing the time interval between said atrial and ventricular pacing pulses in dependence on said directions of variation of said successive impedance changes.

2. A system for maximizing stroke volume of a heart through atrioventricular pacing using an implanted cardioverter/pacer emitting pacing pulses, said system comprising:
   a pair of electrodes for connection in proximity to the heart;
   means for measuring successive impedance changes across said electrodes from one heart cycle to the next;
   means for processing said successive impedance changes to detect directions of variation thereof;
   means for issuing atrial and ventricular pacing pulses, separated by a time interval therebetween, to the atria and to the ventricles, respectively, of the heart; and
   means for selectively increasing or decreasing the time interval between said atrial and ventricular pacing pulses in dependence on said directions of variation of said successive impedance changes.

3. The system of claim 2, said means for processing said successive impedance changes comprising a peak-to-peak impedance change detector having an output representing said variations of said successive impedance changes, a last impedance change latch connected to the output of said peak-to-peak impedance change detector for receiving and holding each said successive impedance change, and a comparator having inputs connected to said peak-to-peak impedance change detector and said last impedance change latch, respectively, for issuing a first output when said successive impedance changes are increasing in magnitude, and for issuing a second output when said successive impedance changes are decreasing in magnitude.

4. The system of the claim 3, further comprising counter means for selectively counting in the upward or downward direction so as to develop a count output representing the time interval between said atrial and ventricular pacing pulses, said means for selectively increasing or decreasing the time interval between said atrial and ventricular pacing pulses comprising a control flip-flop having a first output for causing said counter means to count in the upward direction and a second output for causing the counter means to count in the downward direction, and a selector responsive to said first output of said comparator for controlling said control flip-flop to remain in its present state, and responsive to said second output of said comparator for controlling said control flip-flop to change state.

5. The system of claim 4, wherein said peak-to-peak impedance change detector comprises means for issuing a pulse indicating the presence of valid information relative to successive impedance changes, said system further comprising timing means responsive to said pulse for synchronizing said counting of said counter means with said presence of said valid information relative to said successive impedance changes.

6. The system of claim 3, further comprising timing means for synchronizing said processing of successive impedance changes with said selective increasing or decreasing of the time interval between said atrial and ventricular pacing pulses.

7. The system of claim 2, further comprising timing means for synchronizing said processing of said successive impedance changes with said selective increasing or decreasing of the time interval between said atrial and ventricular paces pulses.

8. The system of claim 2, further comprising actuator means for issuing an actuation command signal, said means for processing being responsive to said actuation command signal for processing said successive impedance changes, and said means for selectively increasing or decreasing the time interval between said atrial and ventricular pacing pulses being responsive to said actuation command signal for selectively increasing or decreasing the time interval between said atrial and ventricular pacing pulses.

9. The system of claim 8, wherein said actuator means comprises timer means for issuing, at given time intervals, said actuation command signal.

10. The system of claim 8, further comprising an external command device, and wherein said actuator means comprises reed switch means responsive to said external command device being brought into proximity thereto for issuing said actuation command signal.

11. An implantable cardioverter and atrioventricular pacer comprising, in combination:
   first and second electrodes for connection in proximity to the heart;
   impedance measuring means for measuring successive impedance changes across said electrodes from one heart cycle to the next;
   processing means for detecting directions of variations of said measured impedance changes;
   pulsing means for issuing atrial and ventricular pacing pulses, separated by a time interval therebetween, to the atria and to the ventricles, respectively, of the heart;
   timing means for selectively increasing or decreasing the time interval between the atrial and ventricular pacing pulses;
   detector means for sensing whether the impedance changes across said electrodes are pulsatile; and
   cardioverting means for issuing a pulse of cardioverting energy in the event that said impedance changes are not pulsatile.

12. A method of maximizing stroke volume of a heart through atrioventricular pacing using an implanted cardioverter/pacer emitting atrial and ventricular pacing pulses separated by a time interval therebeween, comprising the steps:
   measuring successive impedance changes across said heart from one heart cycle to the next so as to detect variation in said successively measured impedance changes; and
   selectively increasing or decreasing said time interval between said atrial and ventricular pacing pulses in accordance with said variation of said successively measured impedance changes, as detected during said measuring step;
   whereby to maximize stroke volume of said heart.

13. An apparatus for maximizing stroke volume of a heart through atrioventricular pacing using an implanted cardioverter/pacer emitting atrial and ventricular pacing pulses separated by a time interval therebetween, comprising:
   measuring means for measuring successive impedance changes across said heart from one heart cycle to the next so as to detect variation in said successively measured impedance changes; and
   adjustment means for selectively increasing or decreasing said time interval between said atrial and ventricular pacing pulses in accordance with said variation of said successively measured impedance changes, as measured by said measuring means;
   whereby to maximize stroke volume of said heart.

* * * * *